United States Patent

Neubauer et al.

[11] Patent Number: 4,920,110
[45] Date of Patent: Apr. 24, 1990

[54] PROPARGYL FURAN- AND THIOPHENECARBOXYLATES

[75] Inventors: Hans-Jürgen Neubauer, Mannheim; Wolfgang Seppelt, Bobenheim-Boxheim; Rainer Bürstinghaus, Heidelberg; Peter Hofmeister, Neustadt; Christoph Kuenast, Waldsee, all of Fed. Rep. of Germany

[73] Assignee: BASF Aktiengesellschaft, Ludwigshafen, Fed. Rep. of Germany

[21] Appl. No.: 338,562

[22] Filed: Apr. 14, 1989

Related U.S. Application Data

[63] Continuation of Ser. No. 90,446, Aug. 28, 1987, abandoned.

[30] Foreign Application Priority Data

Aug. 30, 1986 [DE] Fed. Rep. of Germany ....... 3629584
Nov. 29, 1986 [DE] Fed. Rep. of Germany ....... 3640878

[51] Int. Cl.$^5$ ............... A01N 43/02; A01N 43/08; C07D 333/38; C07D 333/32
[52] U.S. Cl. ............ 514/438; 514/445; 514/461; 549/61; 549/62; 549/66; 549/79; 549/499; 549/501
[58] Field of Search ............ 549/61, 64, 66, 71, 549/79, 484, 499, 501; 514/549, 438, 445, 461

[56] References Cited

U.S. PATENT DOCUMENTS 3,996,380 12/1976 Henrick .
4,024,278 5/1977 Henrick .
4,039,680 8/1977 Fujimoto et al. ............... 549/71
4,309,439 1/1982 Ohno et al. .................. 549/79
4,642,368 2/1987 Hofmeister et al. .

OTHER PUBLICATIONS

Chemical Abstracts, vol. 100, No. 25, Jun. 18, 1984, p. 312, Abstract No. 206418j, G. Kellova et al.
Chemical Abstracts, vol. 97, No. 17, Oct. 25, 1982, p. 620, Abstract No. 144109t, A. I. Levchenko et al.

Primary Examiner—Alan Siegel
Attorney, Agent, or Firm—Keil & Weinkauf

[57] ABSTRACT

Propargyl furan- and thiophenecarboxylates of the formulae Ia and Ib

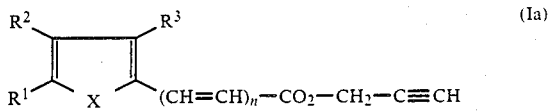

(Ia)

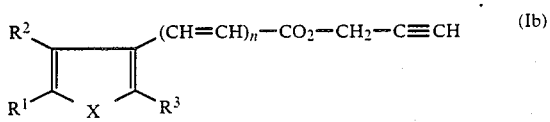

(Ib)

where $R^1$, $R^2$ and $R^3$ are each hydrogen, chlorine, bromine, nitro, $C_1$–$C_4$-alkyl, $C_2$–$C_4$-alkenyl, $C_1$–$C_4$-haloalkyl, $C_2$–$C_4$-haloalkenyl, or phenyl which is unsubstituted or substituted by halogen, $C_1$–$C_4$-alkyl, or $C_1$–$C_4$-alkoxy, X is oxygen or sulfur, n is the integer 0 or 1, and, if X is sulfur, $R^1$, $R^2$ and $R^3$ may furthermore be fluorine, cyano, $C_1$–$C_4$-alkoxy, $C_1$–$C_4$-haloalkoxy, $C_2$–$C_4$-alkenyloxy or $C_2$–$C_4$-haloalkenyloxy, processes for their manufacture, and their use for combating pests.

6 Claims, No Drawings

PROPARGYL FURAN- AND THIOPHENECARBOXYLATES

This application is a continuation of application Ser. No. 090,446, filed on Aug. 28, 1987 now abandoned.

The present invention relates to novel propargyl furan- and thiophenecarboxylates of the general formulae Ia and Ib

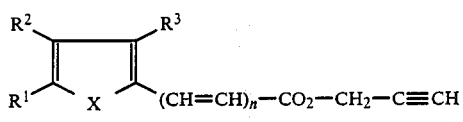

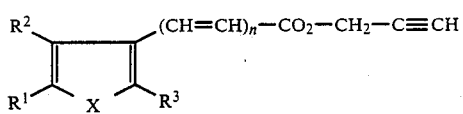

where $R_1$, $R^2$ and $R^3$ are each hydrogen, chlorine, bromine, nitro, $C_1$–$C_4$-alkyl, $C_2$–$C_4$-alkenyl, $C_1$–$C_4$-haloalkyl, $C_2$–$C_4$-haloalkenyl, or phenyl which is unsubstituted or substituted by halogen, $C_1$–$C_4$-alkyl or $C_1$–$C_4$-alkoxy, X is oxygen or sulfur and n is the integer 0 or 1, and, if X is sulfur, $R^1$, $R^2$ and $R^3$ may furthermore be fluorine, cyano, $C_1$–$C_4$-alkoxy, $C_1$–$C_4$-haloalkoxy, $C_2$–$C_4$-alkenyloxy or $C_2$–$C_4$-haloalkenyloxy.

The present invention furthermore relates to pesticides which contain the compounds Ia or Ib as the active ingredient, and a method of controlling pests.

EP-A-156,263, US-A-4,024,278 and US-A-3,996,380 disclose propargyl benzoates and other propargyl carboxylates as pesticides, in particular against mites, but these compounds do not contain a furan or thiophene ring. The action of the known compounds is unsatisfactory.

It is an object of the present invention to provide novel propargyl carboxylates.

We have found that this object is achieved by the novel propargyl furan- and thiophenecarboxylates Ia and Ib defined at the outset and processes for their preparation. We have furthermore found that the compounds Ia and Ib are useful for controlling pests.

The compounds Ia and Ib are obtainable by the following methods:

(a) A furan- or thiophenecarboxylic acid IIa or IIb is reacted with propargyl alcohol (Houben-Weyl, Methoden der org. Chemie, volume VIII, page 516 et seq., Georg-Thieme-Verlag, Stuttgart 1952), and the reaction can be accelerated by adding a catalyst, such as sulfuric acid, a hydrogen halide, a sulfonic acid or an acidic ion exchanger.

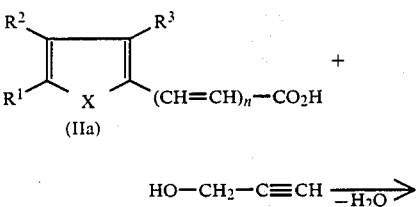

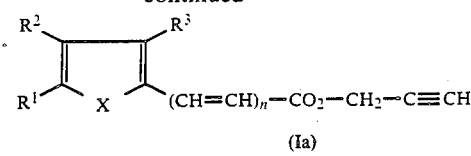

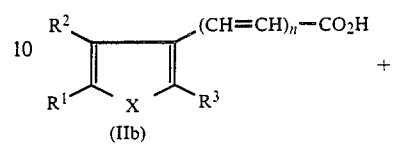

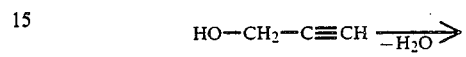

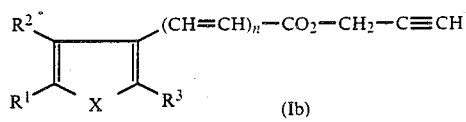

The equilibrium in the esterification can be shifted in the desired direction in a conventional manner, for example by increasing the temperature, distilling off the water azeotropically or binding it to a dehydrating agent, such as sulfuric acid, removing the ester from the reaction mixture or using an excess of one of the two reactants. The reaction is carried out at from 0° to 200° C., preferably from 20° to 150° C., and, in the case of azeotropic distillation, at the particular distillation temperature of the solvent used.

The reaction is advantageously carried out in a solvent or diluent. Examples of suitable substances for this purpose are aliphatic hydrocarbons, such as n-pentane, n-hexane, a mixture of hexane isomers or petroleum ether; aromatic hydrocarbons, such as benzene, toluene, the xylenes or their isomer mixtures or gasoline; and chlorohydrocarbons, such as methyl chloride, chloroform, carbon tetrachloride or 1,2-dichloroethane. Mixtures of these substances may also be used as solvents and diluents.

(b) A furan- or thiophenecarbonyl halide IIIa or IIIb is reacted with propargyl alcohol in the presence of an acid acceptor (cf. Houben-Weyl, Methoden der organischen Chemie, volume VIII, page 543 et seq., Georg-Thieme-Verlag, Stuttgart 1952) at from −30° to 200° C., preferably from 0° to 80° C., according to the following equations:

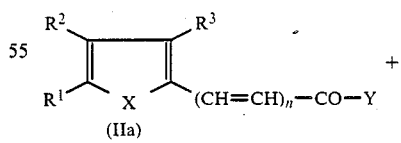

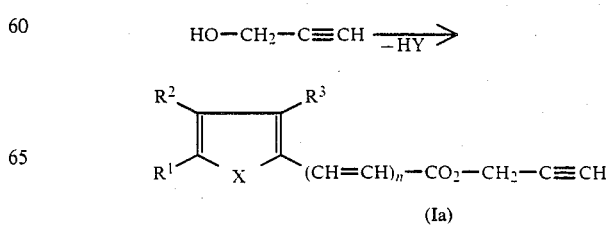

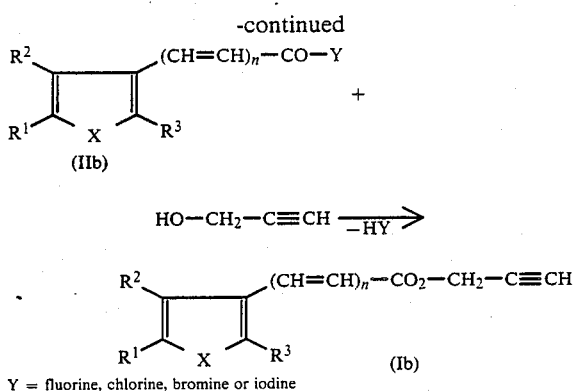

Y = fluorine, chlorine, bromine or iodine

Not less than an equivalent amount of a base is usually added, but the base may also be used in excess or, if required, as a solvent. Examples of suitable bases are hydroxides of alkali metals and alkaline earth metals, such as sodium hydroxide, potassium hydroxide or calcium hydroxide, alcoholates of alkali metals and alkaline earth metals, such as sodium methylate, sodium ethylate, calcium methylate or potassium tert.-butylate, alkali metal and alkaline earth metal hydrides, such as sodium hydride, potassium hydride or calcium hydride, alkali metal and alkaline earth metal carbonates, such as sodium carbonate, potassium carbonate or calcium carbonate, aliphatic amines, such as dimethylamine, triethylamine or diisopropylamine, heterocyclic amines, such as piperidine, piperazine or pyrrolidine, aromatic amines, such as pyridine or pyrrol and, if appropriate, also alkyllithium compounds, such as n-butyllithium.

The reaction is advantageously carried out in a solvent or dilent. Examples of substances which are suitable for this purpose are aliphatic hydrocarbons, such as n-pentane, n-hexane, a mixture of hexane isomers or petroleum ether; chlorohydrocarbons, such as methylene chloride, chloroform, carbon tetrachloride or 1,2-dichlorethane, aromatic hydrocarbons, such as benzene, toluene, the xylenes or their isomer mixtures or gasoline, chloroaromatics, such as chlorobenzene, alcohols, such as methanol, ethanol, n-propanol or isopropanol, ethers, such as diethyl ether, di-n-butyl ether, methyl tert.-butyl ether, tetrahydrofuran or dioxane, ketones, such as acetone, methyl ethyl ketone or methyl isopropyl ketone, nitriles, such as acetonitrile or propionitrile, and aprotic dipolar solvents, such as dimethylformamide, dimethyl sulfoxide or pyridine. Mixtures of these substances can also be used as solvents and diluents.

The furan- and thiophenecarboxylic acids and their acyl halides are known or are obtainable by conventional methods (cf. Heterocyclic Compounds, Thiophene and its derivatives, vol. 44, part 1, page 1 et seq., ed. S. Gronowitz, John Wiley & Sons, New York 1985; Houben-Weyl, loc. cit. page 463 et seq.). Propargyl alcohol is a large-scale industrial product and is commercially available.

The starting materials are usually used in a stoichiometric ratio. However, an excess of one or other of the starting materials may certainly be advantageous in specific cases.

The reaction usually takes place at an adequate rate at above 0° C. Since it proceeds with evolution of heat in some cases, it may be advantageous to provide a means of cooling.

The novel furan- and thiophenecarboxylates can furthermore be prepared by virtually any conventional method of ester synthesis, for example by reacting an appropriate carboxylic anhydride (cf. Houben-Weyl, loc. cit., page 478) with propargyl alcohol, by reacting an appropriate carboxylic acid salt with a propargyl halide or by transesterification reactions (cf. Houben-Weyl, loc. cit., pages 508–628; C. Ferri, Reaktionen der organischen Synthese, page 446 et seq., Georg-Thieme-Verlag, Stuttgart 1978; S. Patai, The Chemistry of Carboxylic Acids and Esters, page 505 et seq., Interscience Publishers, London 1969).

The novel furan and thiophene derivatives where n=1 can furthermore be prepared from appropriately substituted furan- and thiophenecarbaldehydes by condensation with the suitably activated acetate (cf. J. Org. Chem. of USSR (1970), 2309).

The carboxylic acids IIa and IIb required as starting materials are either known or commercially available. Otherwise, they can be prepared by well-known chemical processes (Comprehensive Heterocyclic Chemistry, vol. 4, page 531 et seq; A. R. Katritzky and C. W. Rees, Pergamon Press, 1984; Heterocyclic Compounds, Thiophene and its derivatives, vol. 44, part 1, page 1 et seq., ed. by S. Gronowitz, John Wiley & Sons, New York 1985; The Chemistry of Heterocyclic Compounds, vol. 44, 3, Thiophene and its derivatives, page 565 et seq., John Wiley & Sons, 1986). The carbonyl chlorides used in some of the examples below were obtained from the corresponding carboxylic acids, in some cases according to Houben-Weyl, loc. cit., page 463 et seq.

Specifically, $R^1$, $R^2$ and $R^3$ are each hydrogen, chlorine or bromine, nitro, $C_1$–$C_4$-alkyl, such as methyl, ethyl, n-propyl, isopropyl, n-butyl, isobutyl, sec-butyl or tert.-butyl, preferably methyl or ethyl, particularly preferably methyl, $C_2$–$C_4$-alkenyl, such as ethenyl, prop-1-en-1-yl, prop-2-en-1-yl, but-1-en-1-yl, but-2-en-1-yl or but-3-en-1-yl, preferably ethenyl, $C_1$–$C_4$-haloalkyl, preferably $C_1$- or $C_2$-fluoro- or chloroalkyl, such as fluoromethyl, difluoromethyl, trifluoromethyl, chloromethyl, dichloromethyl, trichloromethyl, 2,2,2-trifluoroethyl or 2,2,2-trichloroethyl, $C_2$–$C_4$-haloalkenyl, preferably $C_2$–$C_4$-fluoro- or chloroalkenyl, phenyl, halophenyl, preferably fluoro- or chlorophenyl, such as 2-fluorophenyl, 4-fluorophenyl, 2,4-difluorophenyl, 2,4,6-trifluoromethyl, 2-chlorophenyl, 4-chlorophenyl, 2,4-dichlorophenyl, 2,4,6-trichlorophenyl or 2-chloro-4-fluorophenyl, $C_7$–$C_{10}$-alkylphenyl, such as 2-methylphenyl, 4-methylphenyl, 2,4-dimethylphenyl, 2,4,6-trimethylphenyl, 2-ethylphenyl, 4-ethylphenyl, 2,4-diethylphenyl, 2-ethyl-4-methylphenyl or 4-ethyl-2-methylphenyl, $C_7$–$C_{10}$-alkoxyphenyl, such as 2-methoxyphenyl, 4-methoxyphenyl, 2,4-dimethoxyphenyl, 2,4,6-trimethoxyphenyl, 2-ethoxyphenyl, 4-ethoxyphenyl, 2,4-diethoxyphenyl, 2-ethoxy-4-methoxyphenyl or 4-ethoxy-2-methoxyphenyl, X is oxygen, sulfur, and n is 0 or 1, and, if X is sulfur, $R^1$, $R^2$ and $R^3$ may furthermore be: fluorine, cyano, $C_1$–$C_4$-alkoxy, preferably methoxy, ethoxy, n-propoxy or isopropoxy, $C_1$–$C_4$-haloalkoxy, preferably $C_1$- or $C_2$-fluoro- or chloroalkoxy, such as fluoromethoxy, difluoromethoxy, trifluoromethoxy, chloromethoxy, dichloromethoxy, trichloromethoxy, 2,2,2-trifluoroethoxy or 2,2,2-trichloroethoxy, $C_2$–$C_4$-alkenyloxy, such as ethenyloxy, prop-1-en-1-yloxy, prop-2-en-1-yloxy, but-1-en-1-yloxy, but-2-en-1-yloxy or but-3-en-1-yloxy, and $C_2$–$C_4$-haloalkenyloxy, preferably $C_2$–$C_4$-fluoro- or chloralkenyloxy.

The propargyl furan- and thiophenecarboxylates of the general formulae Ia and Ib are suitable for effectively controlling pests from the class consisting of insects, arichnids and nematodes. They can be used as pesticides in crop protection, in the hygiene and veterinary sectors and for the protection of stored goods.

In contrast to most of the conventional active ingredients which, as contact or ingested poisons, kill, incapacitate or repel the animals, most of the compounds of the formula I intervene in the hormonal system of the animal organism. In the case of insects, for example, the transformation to the imago, the laying of viable eggs and the development of normal laid eggs are disturbed and the sequence of generations thus interrupted. The novel active ingredients are virtually completely nontoxic for vertebrates. Most of the compounds of the formula I are moreover readily degraded to substances which occur in nature and are further decomposed by microorganisms.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebra, Ostrinia nubilalis, Loxostege sticticalis, Ephestia kuehniella, Chilo suppressalis, Galleria mellonella, Malacosma neustria, Dendrolimus pini, Thaumatopoea pityocampa, Phalera bucephela, Cheimatobia brumata, Hibernia defoliaria, Bupalus pinarius, Hyphantria cunea, Agrotis segetum, Agrotis ypsilon, Barathra brassicae, Cirphis unipuncta, Prodenia litura, Laphygma exigua, Panolis flammea, Earis insulana, Plusia gamma, Alabama argillacea, Lymantria dispar, Lymantria monacha, Pieris brassicae,* and *Aporia crataegi;* examples from the Coleoptera order are *Blitophaga undata, Melanotus communis, Limonius californicus, Agriotes lineatus, Agriotes obscurus, Agrilus sinuatus, Meligethes aeneus, Atomaria linearis, Epilachna varicestris, Phyllopertha horticola, Popillia japonica, Melolontha melolontha, Melolontha hippocastani, Amphimallus solstitialis, Crioceris aspargi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorium, Anthonomus grandis, Ceuthorrhynchus assimilis, Ceuthorrhyncus napi, Sitophilus granaria, Anisandrus dispar, Ips typographus,* and *Blastophagus piniperda;* examples from the Diptera order are *Lycoria pectoralis, Mayetiola destructor, Dasyneura brassicae, Contarinia tritici, Haplodiplosis equestris, Tipula paludosa, Tipula oleraces, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae, Pegomya hyoscyami, Anopheles maculipennis, Culex pipiens, Aedes aegypti, Aedes vexans, Tabanus bovinus, Tipula paludosa, Musca domestica, Fannia canicularis, Muscina stabulans, Glossina morsitans, Oestrus ovis, Chrysomya macellaria, Chrysomya hominivorax, Lucilia cuprina, Lucilia sericata,* and *Hypoderma lineata;* examples from the Hymenoptera order are *Athalia rosae, Hoplocampa minuta, Monomorium pharanois, Solenopsis geminata,* and *Atta sexdens;* examples from the Heteroptera order are *Nezara viridula, Eurygaster integriceps, Blissus leucopterus, Dysdercus cingulatus, Dysdercus intermedius, Piesma quadrata,* and *Lygus pratensis;* examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysaphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordimannianae, Dreyfusia piceae, Adelges laricis,* and *Viteus vitifolii;* examples from the Isoptera order are *Reticulitermes lucifugus, Calotermes flavicollis, Leucotermes flavipes,* and *Termes natalensis;* examples from the Orthoptera order are *Forficula auricularia, Acheta domestica, Gryllotalpa gryllotalpa, Tachycines asynamorus, Locusta migratoria, Stauronotus maroccanus, Schistocerca peregrina, Nomadacris septemfasciata, Melanoplus spretus, Melanoplus femur-rubrum, Blatta orientalis, Blattella germanica, Periplaneta americana,* and *Blabera gigantea.*

Examples of mites and ticks (Acarina) belonging to the Arachnida class are *Tetranychus telarius, Tetranychus atlanticus, Tetranychus pacificus, Paratetranychus pilosus, Bryobia praetiosa, Ixodes ricinus, Ornithodorus moubata, Amblyomma americanum, Dermacentor silvarum,* and *Boophilus microplus.*

Examples from the Nemathelminthes class are rootknot nematodes, e.g., *Meloidogyne incognita, Meloidogyne hapla,* and *Meloidogyne javanica,* cyst-forming nematodes, e.g., *Heterodera rostochiensis, Heterodera schachtii, Heterodera avenae, Heterodera glycines,* and *Heterodera trifolii,* and stem and leaf eelworms, e.g., *Ditylenchus dipsaci, Ditylenchus destructor, Pratylenchus neglectus, Pratylenchus penetrans, Pratylenchus goodeyi, Pratylenchus curvitatus* and *Tylenchorhynchus dubius, Tylenchorhynchus claytoni, Rotylenchus robustus, Heliocotylenchus multicinctus, Radopholus similis, Belonolaimus longicaudatus, Longidorus elongatus,* and *Trichodorus primitivus.*

The active ingredients may be applied as such, in the form of formulations or application forms prepared therefrom, for instance directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts or ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

The formulations contain from 0.1 to 95, and preferably 0.5 to 90, % by weight of active ingredient.

Examples of formulations are given below.

I. 3 parts by weight of compound no. 1 is intimately mixed with 97 parts by weight of particulate kaolin. A dust is obtained containing 3% by weight of the active ingredient.

II. 30 parts by weight of compound no. 5 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 10 parts by weight of compound no. 13 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzene-sulfonic acid, and 2 parts by weight of the adduct of 40 moles of ethylene oxide and 1 mole of castor oil.

IV. 20 parts by weight of compound no. 14 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

V. 80 parts by weight of compound no. 16 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

The active ingredient concentrations in the ready-to-use formulations may vary within a wide range. Generally, they are from 0.0001 to 10, and preferably 0.01 to 1, %. The general ingredients may also successfully be used in the ultra-low-volume method, where it is possible to apply formulations containing more than 95 wt% of active ingredient, or even the 100% active ingredient (without additives).

In the open, the amounts applied range from 0.02 to 10, and preferably 0.08 to 3.0 kg/ha.

There may be added to the active ingredients (if desired, immediately before use (tankmix)) oils of various types, herbicides, fungicides, other insecticides and bactericides. These agents may be added to the active ingredients according to the invention in a weight ratio of from 1:10 to 10:1.

Examples of active ingredients which may be admixed are as follows: 1,2-dibromo-3-chloropropane, 1,3-dichloropropene, 1,3-dichloropropene+1,2-dichloropropane, 1,2-dibromoethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propion aldehyde-O-(methylcarbamoyl)-oxime, S-methyl-N-[(methylcarbamoyl)-oxy]-thioacetimidate, methyl-N',N'-dimethyl-N-[(methylcarbamoyl)-oxy]-1-thiooxamidate, N-(2-methyl-4-chlorophenyl)-N'N'-dimethylformamidine, tetrachlorothiophene, 1-(2,6-difluorobenzyl)-3-(4-chlorophenyl)-urea, O,O-dimethyl-O-(p-nitrophenyl)-phosphorothioate, O,O-diethyl-O-(p-nitrophenyl)-phosphorothioate, O-ethyl-O-(p-nitrophenyl)-phenyl-phosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)- phenyl]-phosphorothioate, O-ethyl-S-phenylethyl-phosphonodithioate, O,O-diethyl-[2-chloro-1-(2,4-dichlorophenyl)-vinyl]-phosphate, O,O-dimethyl-[-2-chloro-1-(2,4,5-trichlorophenyl)]-vinylphosphate, 0,0-dimethyl-S-(1-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethyl-phosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethyl-S-(2-ethylsulfynylethyl)-phosphorothioate, O,O-diethyl-S-(2-ethylthioethyl)-phosphorothioate, O,O-diethyl-S-(2-ethylsulfynylethyl)-phosphorothioate, O,O-diethylthiophosphoryliminophenyl-acetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5[4H]-onyl-(4)-methyl]-phosphorodithioate, O,O-diethyl-O-[3,5,6-trichloropyridyl-(2)]-phosphorothioate, 0,0-diethyl-O-(2-pyrazinyl)-phosphorothioate, O,O-diethyl-O-[2-isopropyl-4-methylpyrimidinyl-(6)]-phosphorothioate, O,O-diethyl-O-[2-(diethylamino)-6-methyl-4-pyrimidinyl]-thionophosphate, O,O-dimethyl-S-(4-oxo-1,2,3-benzotriazin-3-[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoramidothioate, O,S-dimethyl-N-acetylphosphoramidothioate, alpha-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-2,4,3-benzodioxathiepine-3-oxide, pyrethrins, DL-2-allyl-3-methyl-cyclopenten-(2)-on)-on-(1)-yl-(4)-DL-cis,trans-chrysanthemate, 5-benzylfuryl-(3)-methyl-DL-cis,trans-chrysanthemate, 3-phenoxybenzyl(±)-cis,trans-2,2-dimethyl-3-(2,2-dichlorovinyl)-cyclopropanecarboxylate, alpha-cyano-3-phenoxybenzyl(±)-cis,trans-2,2-dimethyl-3-(2,2-dichlorovinyl)-cyclopropanecarboxylate, (s)-alpha-cyano-3-phenoxybenzylcis(1R,3R)-2,2-dimethyl-3-(2,2-dibromovinyl)-cyclopropanecarboxylate, 3,4,5,6-tetrahydrophthalimidoethyl-DL-cis,trans-chrysanthemate, 2-methyl-5-(2-propynyl)-3-furylmethyl-chrysanthemate, and alpha-cyano-3-phenoxybenzyl-alpha-isopropyl-4-chlorophenylacetate.

Examples illustrating the preparation of propargyl furancarboxylates Ia and Ib according to the invention.

Compound no. 5 in Table 1 below

A solution of 1.8 g of propargyl alcohol in 15 ml of absolute pyridine was cooled to 5° C. and 5.2 g of 5-chlorofuran-2-carboxylic chloride was added in portions. The mixture was stirred for 12 hours at room temperature and then poured into 100 ml of icewater; the pH was adjusted to 2 with concentrated hydrochloric acid. The mixture was extracted three times with ether, and the combined extracts were washed with a 10% strength sodium bicarbonate solution and water. After drying over sodium sulfate, removal of the solvent under reduced pressure and recrystallization from methanol, 2.2 g of propargyl 5-chlorofuran-2-carboxylate of melting point 58° to 60° C. was obtained.

Compound no. 14 in Table 1 below

A solution of 11.5 g of 3-(5-methylfuran-2-yl)-propenyl chloride in 30 ml of absolute tetrahydrofuran was cooled to 0° to 5° C., and 4.2 g of propargyl alcohol and 20 ml of pyridine were added. The mixture was stirred for 12 hours at room temperature, the precipitated hydrochloride was filtered off and concentrated under reduced pressure, and the concentrate taken up in 200 ml of ethyl acetate and 50 ml of water. After washing three times with water, drying over $Na_2SO_4$ and removal of the solvent under reduced pressure, the residue was purified chromatographically (toluene/ethyl acetate=½). There was obtained 10.9 g of propargyl 3-(5-methylfuran-2-yl)-propenoate; refractive index $n_D^{26}=1.578$.

Compound no. 22 in Table 1 below 6.8 g of propargyl alcohol was dissolved in 20 ml of absolute pyridine. After 17.0 g of 2.5-dimethylfuran-3-carboxyl chloride had been added at 5° C. at most, the mixture was stirred for 8 hours at room temperature. 100 ml of diethyl ether was added. After suction filtration, the filtrate was concentrated under reduced pressure. The residue was taken up in 150 ml of ethyl acetate and extracted with water, and the organic phase was dried over sodium sulfate. After removal of the solvent under reduced pressure, the product was recrystallized from n-propanol/water. There was obtained 12.5 g of propargyl 2,5-dimethylfuran-3-carboxylate of melting point 35° to 37° C.

TABLE 1

| Example No. | Structure corresp. to formula | n | $R^1$ | $R^2$ | $R^3$ | X | Physical data |
|---|---|---|---|---|---|---|---|
| 1 | Ia | 0 | H | H | H | O | oil |
| 2 | Ia | 0 | $CH_3$ | H | H | O | $n_D^{22}$: 1.512 |
| 3 | Ia | 0 | H | $CH_3$ | H | O | |
| 4 | Ia | 0 | H | H | $CH_3$ | O | |
| 5 | Ia | 0 | Cl | H | H | O | mp: 58–60° C. |
| 6 | Ia | 0 | H | H | Cl | O | |
| 7 | Ia | 0 | Br | H | H | O | mp: 87–89° C. |
| 8 | Ia | 0 | H | H | Br | O | |
| 9 | Ia | 0 | $NO_2$ | H | H | O | mp: 86–87° C. |

TABLE 1-continued

| Example No. | Structure corresp. to formula | n | R¹ | R² | R³ | X | Physical data |
|---|---|---|---|---|---|---|---|
| 10 | Ia | 0 | CH₂Cl | H | H | O | |
| 11 | Ia | 0 | 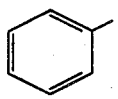 | H | H | O | |
| 12 | Ia | 0 | 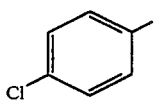 | H | H | O | |
| 13 | Ia | 1 | H | H | H | O | mp: 44–45° C. |
| 14 | Ia | 1 | CH₃ | H | H | O | $n_D^{26}$: 1.578 |
| 15 | Ia | 1 | H | H | CH₃ | O | |
| 16 | Ia | 1 | Cl | H | H | O | mp: 54–55° C. |
| 17 | Ia | 1 | H | H | Cl | O | |
| 18 | Ia | 1 | Br | H | H | O | |
| 19 | Ia | 1 | 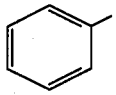 | H | H | O | |
| 20 | Ib | 0 | H | H | H | O | oil |
| 21 | Ib | 0 | CH₃ | H | H | O | |
| 22 | Ib | 0 | CH₃ | H | CH₃ | O | mp: 35–37° C. |
| 23 | Ib | 0 | CH₃ | CH₃ | CH₃ | O | mp: 52–54° C. |
| 24 | Ib | 0 | H | H | CH₃ | O | $n_D^{22}$: 1.497 |
| 25 | Ib | 0 | Cl | H | H | O | |
| 26 | Ib | 0 | H | H | Cl | O | |
| 27 | Ib | 0 | 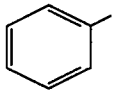 | H | H | O | |
| 28 | Ib | 1 | CH₃ | H | CH₃ | O | |
| 29 | Ib | 1 | H | H | H | O | |
| 30 | Ib | 1 | H | H | H | O | |

Examples illustrating the preparation of propargyl thiophenecarboxylates Ia and Ib according to the invention.

Compound no. 4 in Table 2 below

A solution of 2.2 g of propargyl alcohol in 35 ml of absolute pyridine was cooled to 5° C. At this temperature, 8.6 g of 5-bromothiophene-2-carboxyl chloride was added in portions. The mixture was stirred for 8 hours at room temperature and poured into 100 ml of icewater, and the pH was adjusted to 2 with concentrated HCl. The aqueous phase was extracted three times with ether and the combined extracts were washed with 10% strength NaHCO₃ solution and water. Drying over Na₂SO₄ and removal of the solvent gave a residue which, after recrystallization from n-propanol/water, yielded 4.2 g of propargyl 5-bromothiophene-2-carboxylate of melting point 65° to 68° C.

Compound no. 25 in Table 2 below

At 10° C., 0.9 g of sodium hydride was added to a solution of 6.2 g of 3-(3-methylthiophen-2-yl)-propenoic acid in 100 ml of absolute DMF. When no more hydrogen evolved, 4.9 g of propargyl bromide was dripped in at room temperature and the mixture was then heated at 50° C. for 3 hours. The reaction mixture was poured onto icewater, the aqueous phase was extracted three times with ethyl acetate, and the combined organic extracts were dried over Na₂SO₄. After removal of the solvent under reduced pressure, the residue was recrystallized from ethanol. There was obtained 3.9 g of propargyl 3-(3-methylthiophen-2-yl)-propenoate of melting point 84' to 86° C.

Compound no. 45 in Table 2 below 4.7 g of propargyl alcohol was dissolved in 50 ml of absolute pyridine. At 0° C. at most, 18.4 g of 3-(2,3-dichlorothiophen-4-yl)-propenoyl chloride was added and the reaction batch was stirred for 12 hours at room temperature. 50 ml of diethyl ether was added, the precipitated pyridine hydrochloride was filtered off and the filtrate concentrated under reduced pressure. The residue was taken up in 150 ml of ethyl acetate, the mixture was shaken with water and the organic phase was dried over Na₂SO₄. After removal of the solvent under reduced pressure, the residue was recrystallized from methanol. There was obtained 7.6 g of propargyl 3-(2,3-dichlorothiophen-4-yl)-propenoate of melting point 84° to 86° C.

TABLE 2

| Example No. | Structure corresp. to formula | n | R¹ | R² | R³ | X | Physical data |
|---|---|---|---|---|---|---|---|
| 1 | Ia | 0 | H | H | H | S | viscous oil |
| 2 | Ia | 0 | Cl | H | H | S | mp.: 37–39° C. |
| 3 | Ia | 0 | NO₂ | H | H | S | $n_D^{23}$: 1.5860 |
| 4 | Ia | 0 | Br | H | H | S | mp.: 65–68° C. |
| 5 | Ia | 0 | Br | Br | H | S | mp.: 60–63° C. |
| 6 | Ia | 0 | H | H | CH₃ | S | $n_D^{23}$: 1.5512 |
| 7 | Ia | 0 | H₃C— | H | H | S | $n_D^{22}$: 1.5501 |
| 8 | Ia | 0 | H | Br | H | S | mp.: 45–47° C. |
| 9 | Ia | 0 | CN | H | H | S | |
| 10 | Ia | 0 | CH₃ | H | CH₃ | S | |
| 11 | Ia | 0 | CH=CH₂ | H | H | S | |
| 12 | Ia | 0 | CH₂—CH₃ | H | H | S | |
| 13 | Ia | 0 | phenyl | H | H | S | |
| 14 | Ia | 0 | 4-Cl-phenyl | H | H | S | |
| 15 | Ia | 0 | CH₃O | H | H | S | |
| 16 | Ia | 0 | H | H | CH₃O | S | |
| 17 | Ia | 0 | H | H | Cl | S | |
| 18 | Ia | 0 | Cl | H | Cl | S | |
| 19 | Ia | 0 | Cl | Cl | H | S | |
| 20 | Ia | 0 | Cl | Cl | Cl | S | |
| 21 | Ia | 1 | H | H | H | S | $n_D^{20}$: 1.6068 |
| 22 | Ia | 1 | H | Br | H | S | mp.: 93–95° C. |
| 23 | Ia | 1 | Cl | H | H | S | mp.: 51–53° C. |
| 24 | Ia | 1 | CH₃ | H | H | S | mp.: 38–40° C. |
| 25 | Ia | 1 | H | H | CH₃ | S | mp.: 74–78° C. |
| 26 | Ia | 1 | NO₂ | H | H | S | |
| 27 | Ia | 1 | Br | H | H | S | mp.: 68–70° C. |
| 28 | Ia | 1 | phenyl | H | H | S | |
| 29 | Ia | 1 | 4-Cl-phenyl | H | H | S | |
| 30 | Ia | 1 | CN | H | H | S | |
| 31 | Ia | 1 | Cl | Cl | H | S | |
| 32 | Ib | 0 | H | H | H | S | $n_D^{22}$: 1.5494 |
| 33 | Ib | 0 | CH₃ | H | H | S | |
| 34 | Ib | 0 | Cl | Cl | H | S | mp.: 48–50° C. |
| 35 | Ib | 0 | H | CH₃ | H | S | |
| 36 | Ib | 0 | H | Br | H | S | |
| 37 | Ib | 0 | NO₂ | H | H | S | |
| 38 | Ib | 0 | CH₃O | H | CH₃ | S | |
| 39 | Ib | 0 | Cl | H | Cl | S | |
| 40 | Ib | 0 | Br | H | H | S | |
| 41 | Ib | 0 | CH₃ | CH₃ | H | S | |
| 42 | Ib | 1 | H | H | H | S | $n_D^{22}$: 1.6053 |
| 43 | Ib | 1 | CH₃ | H | H | S | |
| 44 | Ib | 1 | CH₃ | H | CH₃ | S | |
| 45 | Ib | 1 | Cl | Cl | H | S | mp.: 84–86° C. |
| 46 | Ib | 1 | Cl | H | H | S | |
| 47 | Ib | 1 | H | Br | H | S | |
| 48 | Ib | 1 | Br | Br | H | S | |

Use example

Ovicidal action on Dysdercus intermedius (cotton stainer)

Pieces of double-sided adhesive tape (about 0.8 cm) were stuck to the top edge of plastic plant markers. 24 hours before commencement of the experiment, eggs of the cotton stainer contained in a vessel were attached to the adhesive strips by dipping the markers into the vessel. The eggs were then dipped for 5 seconds into aqueous formulations of the active ingredients and excess liquid was allowed to drip off onto filter paper, care being taken to prevent the eggs coming into contact with the paper. The markers were then placed in plastic trays (adhesive strip at the top). Half a roll of absorbent cotton was moistened with water and placed in each beaker to prevent drying out, and the trays were covered with a glass plate. Assessment took place after 8 days (control bugs hatched).

In this experiment, compounds nos. 2, 7 and 16 achieved 80% kill at an application rate of 0.02 wt%, and compounds nos. 1 and 5 the same kill at a rate of 0.002 wt%. The lethal dose for compounds nos. 13 and 14 was 0.002 wt%.

We claim:

1. Propargyl furan- and thiophenecarboxylates of the formulae Ia and Ib

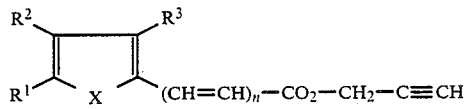
(Ia)

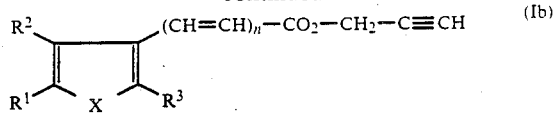
(Ib)

where $R^1$, $R^2$ and $R^3$ are each hydrogen, chlorine, bromine, $C_1$-$C_4$-alkyl, $C_2$-$C_4$-alkenyl, $C_1$-$C_4$-haloalkyl, $C_2$-$C_4$-haloalkenyl, or phenyl which is unsubstituted or substituted by halogen, $C_1$-$C_4$-alkyl, or $C_1$-$C_4$-alkoxy, X is oxygen or sulfur, n is the integer 1, and, if X is sulfur, $R^1$, $R^2$ and $R^3$ may furthermore be fluorine, cyano, $C_1$-$C_4$-alkoxy, $C_1$-$C_4$-haloalkoxy, $C_2$-$C_4$-alkenyloxy or $C_2$-$C_4$-haloalkenyloxy.

2. Propargyl furan- and thiophenecarboxylates of the formulae Ia and Ib as set forth in claim 1, wherein $R^1$ is hydrogen, chlorine, bromine, methyl, ethyl, ethenyl, chloromethyl, phenyl or p-chlorophenyl, and $R^2$ and $R^3$ are each hydrogen, chlorine, bromine or methyl, X is oxygen or sulfur, n is the integer 1, and, if X is sulfur, $R^1$ may furthermore be cyano or methoxy and $R^3$ may be furthermore be methoxy.

3. Propargyl furan- and thiophenecarboxylates of the formulae Ia and Ib as set forth in claim 1, where $R^1$ is hydrogen, chlorine, bromine, nitro or methyl, $R^2$ is hydrogen, chlorine, bromine or methyl, $R^3$ is hydrogen or methyl, X is oxygen or sulfur, and n is 1.

4. A pesticide containing an effective amount of a propargyl furan- or thiophenecarboxylate of the formulae Ia or Ib as set forth in claim 1, and conventional carriers.

5. A pesticide as set forth in claim 3, containing from 0.1 to 95 wt% of a propargyl furan- or thiophenecarboxylate of the formulae Ia or Ib.

6. A process for combating insects, mites, ticks and nematodes, wherein the insects, mites, ticks and nematodes, or the areas and/or rooms to be kept free from them are treated with an effective amount of a propargyl furan- or thiophenecarboxylate of the formula Ia or Ib as defined in claim 1.

* * * * *